United States Patent
Ebinuma et al.

(10) Patent No.: US 9,097,714 B2
(45) Date of Patent: Aug. 4, 2015

(54) METHOD FOR DIAGNOSING MALIGNANT TUMOR

(75) Inventors: Hiroyuki Ebinuma, Ryugasaki (JP); Kohei Takubo, Ryugasaki (JP); Masanao Matsuo, Ryugasaki (JP); Isamu Fukamachi, Ryugasaki (JP); Hideaki Bujo, Chiba (JP); Chiaki Nakaseko, Chiba (JP); Yasushi Saito, Chiba (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 13/512,903

(22) PCT Filed: Dec. 15, 2010

(86) PCT No.: PCT/JP2010/072521
§ 371 (c)(1),
(2), (4) Date: May 31, 2012

(87) PCT Pub. No.: WO2011/074594
PCT Pub. Date: Jun. 23, 2011

(65) Prior Publication Data
US 2013/0029363 A1 Jan. 31, 2013

(30) Foreign Application Priority Data

Dec. 16, 2009 (JP) ................. 2009-285492
May 26, 2010 (JP) ................. 2010-120390

(51) Int. Cl.
G01N 33/574 (2006.01)
G01N 21/64 (2006.01)
G01N 21/47 (2006.01)
G01N 21/76 (2006.01)
G01N 33/92 (2006.01)

(52) U.S. Cl.
CPC ........ *G01N 33/574* (2013.01); *G01N 33/57426* (2013.01); *G01N 33/92* (2013.01); *G01N 2800/52* (2013.01); *G01N 2800/54* (2013.01)

(58) Field of Classification Search
CPC ........... C12Q 1/6886; C12Q 2600/158; C12Q 1/6883; C12Q 2600/112; C12Q 2600/156; C12Q 2600/118; A61K 2300/00
See application file for complete search history.

(56) References Cited

U.S. PATENT DOCUMENTS

| 5,665,872 | A | 9/1997 | Saito et al. | |
|---|---|---|---|---|
| 2006/0240426 | A1* | 10/2006 | Orntoft et al. | 435/6 |
| 2011/0091993 | A1* | 4/2011 | Matsuo et al. | 436/501 |
| 2011/0177610 | A1 | 7/2011 | Matsuo et al. | |

FOREIGN PATENT DOCUMENTS

| EP | 2 256 497 A1 | 12/2010 |
|---|---|---|
| JP | 9 163988 | 6/1997 |
| WO | WO 03/010336 A2 | 2/2003 |
| WO | WO 03/010336 A3 | 2/2003 |
| WO | WO 2005/015236 A2 | 2/2005 |
| WO | WO 2005/015236 A3 | 2/2005 |
| WO | 2008 155891 | 12/2008 |
| WO | 2009 116268 | 9/2009 |
| WO | WO 2011/027308 A1 | 3/2011 |
| WO | WO 2011/027308 A8 | 3/2011 |

OTHER PUBLICATIONS

Matsuo et al (Japan Atherosclerosis Society, 2008, abstract 155.*
Hirayama, S., "Differential Expression of LR11 during Proliferation and Differentiation of Cultured Neuroblastoma Cells," Biochemical and Biophysical Research Communications, vol. 275, No. 2, pp. 365-373, (2000).
Jiang, M., et al., "Naimaku Heikatsukin Saibo no Tokuiteki Hatsugen Idenshi LR11 wa Keishitsu Henkan o Seigyo suru," The 38th Japan Atherosclerosis Society Annual Meeting, vol. 38, p. 272, (Jul. 1, 2006).
Matsuo, T., et al., "Development of an ELISA System for the Quantification of Soluble LR11," Annual Scientific Meeting of the Japan Atherosclerosis Society Program Shorokushu, vol. 40th, p. 239, (Jun. 27, 2008) (with English translation).
Ohwada, C., et al., "Prognostic impact of serum soluble LR11 on acute leukemias," The Japanese Journal of Clinical Hematology, vol. 51, No. 9, p. 1016, (Sep. 30, 2010).
Takeuchi, M., et al., "LR11 is a novel surface marker for normalLeukocyte and leukemia cells," The Japanese Journal of Clinical Hematology, vol. 51, No. 9, p. 1015, (Sep. 30, 2010).
Sakai, S., et al., "Soluble LR11 is a novel biomarker for acute leukemias," The Japanese Journal of Clinical Hematology, vol. 51, No. 9, p. 926, (Sep. 30, 2010).
Yamazaki, H., et al., "Elements of Neural Adhesion Molecules and a Yeast Vacuolar Protein Sorting Receptor Are Present in a Novel Mammalian Low Density Lipoprotein Receptor Family Member," The Journal of Biological Chemistry, vol. 271, No. 40, pp. 24761-24768 (1996).
Kanaki, T., et al., "Expression of LR11, a Mosaic LDL Receptor Family Member, Is Markedly Increased in Atherosclerotic Lesions," Arterioscler Thromb Vasc. Biol, pp. 2687-2695, (Nov. 1999).
Jiang, M., et al., "Ang II-stimulated migration of vascular smooth muscle cells is dependent on LR11 in mice," The Journal of Clinical Investigation, vol. 118, No. 8, pp. 2733-2746, (Aug. 2008).
Matsuo, M., et al., Development of an Immunoassay for the Quantification of Soluble LR11, a Circulating Marker of Atherosclerosis, Clinical Chemistry, vol. 55:10, pp. 1801-1808, (2009).

(Continued)

*Primary Examiner* — Sean Aeder
*Assistant Examiner* — Julie Wu
(74) *Attorney, Agent, or Firm* — Oblon, McClelland, Maier & Neustadt, L.L.P.

(57) ABSTRACT

To provide a method and a diagnostic kit for determining the presence of a malignant tumor or the severity thereof, a method for selecting a therapeutic method therefor or evaluating the effect of the therapeutic method, or a method for estimating the risk of recurrence of the malignant tumor or determining the presence or absence of the recurrence.
The method for determining the presence of a malignant tumor or the severity thereof, method for selecting a therapeutic method therefor or evaluating the effect of the therapeutic method, or method for estimating the risk of recurrence of the malignant tumor or the presence or absence of the recurrence is characterized by including 1) a step of measuring the concentration and/or quantity of soluble LR11 in a sample originating from a subject and 2) a step of comparing the value measured above with a measurement value of soluble LR11 obtained from a healthy subject group.

10 Claims, 3 Drawing Sheets

(56) References Cited

OTHER PUBLICATIONS

International Search Report Issued Feb. 8, 2011 in PCT/JP10/072521 Filed Dec. 15, 2010.
U.S. Appl. No. 13/810,377, filed Jan. 15, 2013, Ebinuma, et al.
Extended European Search Report issued Nov. 7, 2012 in European Patent Application No. 10837620.3.
Yanjuan Zhu, et al., "LR11, an LDL Receptor Gene Family Member, Is a Novel Regulator of Smooth Muscle Cell Migration", Circulation Research, vol. 94, No. 6, XP009134177, Apr. 1, 2004, pp. 752-758 (plus cover page).
Kenji Ohwaki, et al., "A Secreted Soluble Form of LR11, Specifically Expressed in Intimal Smooth Muscle Cells, Accelerates Formation of Lipid-Laden Macrophages", Arteriosclerosis, Thrombosis, and Vascular Biology, vol. 27, No. 5, XP009134179, May 1, 2007, 13 pages.
Chikako Ohwada, et al., "Prognostic Impact of a Novel Biomarker, Serum Soluble LR11 on Acute Leukemia", Blood, vol. 116, No. 21, XP009164197, Nov. 2010, pp. 1119-1120.
U.S. Appl. No. 14/116,683, filed Nov. 8, 2013, Takubo et al.
Russian Office Actin dated Dec. 16, 2014, in patent application No. 2012129913. (English Translation).
He X, et al., "The potential mechanism of chemosensitive difference between 2 types of ovarian cancer", Saudi med. J., Jul. 2007, vol. 28, No. 7, pp. 1044-1049. (Abstract).

* cited by examiner

SEQUENCE LISTING

```
<160> NUMBER OF SEQ ID NOS: 1

<210> SEQ ID NO 1
<211> LENGTH: 551
<212> TYPE: PRT
<213> ORGANISM: Artificial
<220> FEATURE:
<223> OTHER INFORMATION: fragment of LR11 peptide
```

<400> SEQUENCE: 1

```
Gln Leu Thr Gly Leu Met Asp Met Lys Ile Phe Tyr Lys Gly Lys Asn
1               5                   10                  15

Thr Gly Ser Asn Ala Cys Val Pro Arg Pro Cys Ser Leu Leu Cys Leu
            20                  25                  30

Pro Lys Ala Asn Asn Ser Arg Ser Cys Arg Cys Pro Glu Asp Val Ser
        35                  40                  45

Ser Ser Val Leu Pro Ser Gly Asp Leu Met Cys Asp Cys Pro Gln Gly
    50                  55                  60

Tyr Gln Leu Lys Asn Asn Thr Cys Val Lys Glu Glu Asn Thr Cys Leu
65                  70                  75                  80

Arg Asn Gln Tyr Arg Cys Ser Asn Gly Asn Cys Ile Asn Ser Ile Trp
                85                  90                  95

Trp Cys Asp Phe Asp Asn Asp Cys Gly Asp Met Ser Asp Glu Arg Asn
                100                 105                 110

Cys Pro Thr Thr Ile Cys Asp Leu Asp Thr Gln Phe Arg Cys Gln Glu
            115                 120                 125

Ser Gly Thr Cys Ile Pro Leu Ser Tyr Lys Cys Asp Leu Glu Asp Asp
        130                 135                 140

Cys Gly Asp Asn Ser Asp Glu Ser His Cys Glu Met His Gln Cys Arg
145                 150                 155                 160

Ser Asp Glu Tyr Asn Cys Ser Ser Gly Met Cys Ile Arg Ser Ser Trp
                165                 170                 175

Val Cys Asp Gly Asp Asn Asp Cys Arg Asp Trp Ser Asp Glu Ala Asn
            180                 185                 190

Cys Thr Ala Ile Tyr His Thr Cys Glu Ala Ser Asn Phe Gln Cys Arg
            195                 200                 205

Asn Gly His Cys Ile Pro Gln Arg Trp Ala Cys Asp Gly Asp Thr Asp
        210                 215                 220

Cys Gln Asp Gly Ser Asp Glu Asp Pro Val Asn Cys Glu Lys Lys Cys
225                 230                 235                 240

Asn Gly Phe Arg Cys Pro Asn Gly Thr Cys Ile Pro Ser Ser Lys His
                245                 250                 255

Cys Asp Gly Leu Arg Asp Cys Ser Asp Gly Ser Asp Glu Gln His Cys
            260                 265                 270

Glu Pro Leu Cys Thr His Phe Met Asp Phe Val Cys Lys Asn Arg Gln
            275                 280                 285

Gln Cys Leu Phe His Ser Met Val Cys Asp Gly Ile Ile Gln Cys Arg
        290                 295                 300

Asp Gly Ser Asp Glu Asp Ala Ala Phe Ala Gly Cys Ser Gln Asp Pro
305                 310                 315                 320

Glu Phe His Lys Val Cys Asp Glu Phe Gly Phe Gln Cys Gln Asn Gly
                325                 330                 335

Val Cys Ile Ser Leu Ile Trp Lys Cys Asp Gly Met Asp Asp Cys Gly
            340                 345                 350

Asp Tyr Ser Asp Glu Ala Asn Cys Glu Asn Pro Thr Glu Ala Pro Asn
            355                 360                 365

Cys Ser Arg Tyr Phe Gln Phe Arg Cys Glu Asn Gly His Cys Ile Pro
        370                 375                 380

Asn Arg Trp Lys Cys Asp Arg Glu Asn Asp Cys Gly Asp Trp Ser Asp
385                 390                 395                 400

Glu Lys Asp Cys Gly Asp Ser His Ile Leu Pro Phe Ser Thr Pro Gly
```

-continued

```
                     405                     410                     415
Pro Ser Thr Cys Leu Pro Asn Tyr Tyr Arg Cys Ser Ser Gly Thr Cys
            420                     425                 430

Val Met Asp Thr Trp Val Cys Asp Gly Tyr Arg Asp Cys Ala Asp Gly
        435                 440                 445

Ser Asp Glu Glu Ala Cys Pro Leu Leu Ala Asn Val Thr Ala Ala Ser
    450                 455                 460

Thr Pro Thr Gln Leu Gly Arg Cys Asp Arg Phe Glu Phe Glu Cys His
465             470                 475             480

Gln Pro Lys Thr Cys Ile Pro Asn Trp Lys Arg Cys Asp Gly His Gln
            485                 490                 495

Asp Cys Gln Asp Gly Arg Asp Glu Ala Asn Cys Pro Thr His Ser Thr
            500             505                 510

Leu Thr Cys Met Ser Arg Glu Phe Gln Cys Glu Asp Gly Glu Ala Cys
        515             520                 525

Ile Val Leu Ser Glu Arg Cys Asp Gly Phe Leu Asp Cys Ser Asp Glu
        530             535             540

Ser Asp Glu Lys Ala Cys Ser
545                 550
```

METHOD FOR DIAGNOSING MALIGNANT TUMOR

FIELD OF THE INVENTION

The present invention relates to a method for determining the presence of a malignant tumor or the severity thereof, a method for selecting a therapeutic method therefor or evaluating the effect of the therapeutic method, or a method for estimating the risk of recurrence of the malignant tumor or the presence or absence of the recurrence, and to a diagnostic kit for the same purposes.

BACKGROUND OF THE INVENTION

In recent years, on annual basis, more than 10 million people have been diagnosed as having a malignant tumor, and more than 7 million people die of malignant tumor, and the numbers tend to increase. Correct diagnosis, appropriate treatment, evaluation of the effect of the treatment, and prediction and prevention of recurrence of malignant tumor are thought to be important factors for malignant tumor patients to survive. Currently, in order to obtain valuable information therefor, histopathological diagnosis, genetic testing, diagnostic imaging, blood-basis clinical tests, etc. are carried out singly or in combination. In particular, the determination of tumor marker level in a blood sample is a convenient and relatively inexpensive testing method.

Malignant tumors are generally classified into carcinoma and sarcoma. According to the new WHO classification, a hematopoietic tumor, which is a type of sarcoma, is generally divided into leukemia and malignant lymphoma. Leukemia is divided into acute leukemia (rapid growing) and chronic leukemia (slow growing), and acute leukemia is divided into acute lymphocytic leukemia (ALL) and acute myeloid leukemia (AML). ALL is further divided, on the basis of cell type, into T-cell ALL and B-cell ALL.

In the case where the blast level in bone marrow is 20% or higher, the condition is diagnosed as AML, and in the case where the blast level in bone marrow is lower than 20%, the condition is diagnosed as myelodysplastic syndrome (MDS).

In the case of acute leukemia (AL), immediate start of the treatment therefor is essential, since it shows rapid progression. When AL or recurrence thereof is suspected, bone marrow cells are analyzed through bone marrow aspiration for definite diagnosis. However, this test cannot be used frequently since it is very invasive to the patients.

In chronic leukemia (CL), which differs from AL in that differentiation and maturation ability is maintained, chronic myeloid leukemia (CML) is classified as a myeloproliferative disorder (MPD), and chronic lymphocytic leukemia (CLL) is classified as a malignant lymphoma. CL does not have specific symptoms and progresses slowly. However, since CL may sometimes become AL (acute conversion) in the long term, periodic observation is required during and after the treatment.

Meanwhile, malignant lymphoma is generally classified into Hodgkin's lymphoma (HL) and non-Hodgkin's lymphoma (NHL).

In Japan, about 90% of malignant lymphoma cases are NHL, and there are often observed follicular lymphoma, which is a low-grade and slow growing lymphoma, and diffuse large B-cell lymphoma, which is a medium-grade and rapid growing lymphoma. The treatment of NHL varies depending on the classified stage and malignancy grade. Among lymphoma cases, particularly, low-grade lymphoma progresses slowly and is less susceptible to treatment, and increase in malignancy and transition to leukemia may occur. Therefore, careful follow-up observation of symptoms of low-grade lymphoma is required.

Malignant lymphoma occurs at lymph nodes as foci. Since lymph nodes are present throughout the body, the focal sites of malignant lymphoma are difficult to find, as compared with the case of leukemia. Particularly in the case of recurrence thereof, specific focal sites are difficult to detect in reality. Therefore, it is very important to determine the focal site and scale of the pathological condition in the body, requiring expensive diagnostic imaging such as CT, MRI, or PET and highly invasive bone marrow aspiration.

In order to assess the expansion and strength of the disease and the effect of the treatment therefor, blood test for lactate dehydrogenase (LDH), C-reactive protein (CRP), $\beta$2-microglobulin, ferritin, soluble interleukin-2 receptor (sIL-2R), etc. is carried out. However, test values for these blood analysis items are known to rise by liver malfunction, kidney malfunction, bacterial infection, and collagen diseases such as rheumatoid arthritis and SLE. Therefore, these test value-raising factors must be carefully taken into consideration when hematopoietic tumor is diagnosed based on the above-described blood analysis items.

In clinical examination, tumor markers such as $\alpha$-fetoprotein, CEA, and CA19-9 are employed to detect carcinomas such as liver cancer, pancreatic cancer, colon cancer, etc. When any of these markers is employed singly, in many cases, organ-specificity and malignant tumor detection sensitivity are insufficient. Thus, a plurality of tumor markers are often assayed in combination, and therefore, there is demand for development of an assay item which can serve as a new tumor marker.

LR11 (LDL receptor relative with 11 ligand-binding repeats) was a novel LDL receptor-like protein identified as having a characteristic structure to the LDL receptor family (Patent Document 1 and Non-Patent Document 1). Expression of LR11 is reported to be promoted particularly in vascular intima thickened sites generated by migration and proliferation of smooth muscle cells (Non-Patent Document 2). Furthermore, the following are also known: soluble LR11 is present in blood of mammals; the level of soluble LR11 of arteriosclerosis disease patients is significantly higher than that of healthy subjects (Patent Document 2); and soluble LR11 level is an independent factor which defines the intima media thickness (IMT) (Non-Patent Document 3). Moreover, there is also known a method for readily and correctly determining the soluble LR11 level in blood and cerebrospinal fluid (Patent Document 3, Non-Patent Document 4).

PRIOR ART DOCUMENTS

Patent Documents

Patent Document 1: JP09-163988 A
Patent Document 2: WO2008155891
Patent Document 3: WO2009116268

Non-Patent Documents

Non-Patent Document 1: J. Biol. Chem. 1996; 271, 24761-24768
Non-Patent Document 2: Arterioscler. Thromb. Vasc. Biol. 1999; 19, 2687-2695
Non-Patent Document 3: J. Clin. Invest. 2008; 118, 2733-2746
Non-Patent Document 4: Clin. Chem. 2009; 55, 1801-1808

SUMMARY OF THE INVENTION

An object of the present invention is to provide a method for determining the presence of a malignant tumor or the severity thereof, a method for selecting a therapeutic method therefor or evaluating the effect of the therapeutic method, or a method for estimating the risk of recurrence of the malignant tumor or the presence or absence of the recurrence. Another object of the present invention is to provide a diagnostic reagent therefor. Still another object of the present invention is to provide a diagnostic kit for the same purposes.

Means for Solving the Problems

The present inventors have carried out extensive studies for the purpose of finding a new malignant tumor marker. Quite surprisingly, the inventors have found that a soluble LR11 is present at a considerably higher concentration in body fluid samples taken from malignant tumor patients than those taken from healthy subjects. The inventors have also found that the soluble LR11 concentration lowers to a normal level through treatment of the malignant tumor and rises again upon recurrence of the malignant tumor, and that soluble LR11 concentration can be employed as a tumor marker useful for determining the presence of a malignant tumor or the severity thereof, for selecting a therapeutic method therefor or evaluating the effect of the therapeutic method, or for estimating the risk of recurrence of the malignant tumor or the presence or absence of the recurrence. The present invention has been accomplished on the basis of these findings.

Accordingly, the present invention provides a method for determining the presence of a malignant tumor or the severity thereof, a method for selecting a therapeutic method therefor or evaluating the effect of the therapeutic method, or a method for estimating the risk of recurrence of the malignant tumor or the presence or absence of the recurrence, characterized in that the method comprises 1) a step of measuring the concentration and/or quantity of soluble LR11 in a sample originating from a subject and 2) a step of comparing the value obtained above with a soluble LR11 value in a sample obtained from a healthy subject group.

The present invention also provides a reagent composition or a kit for determining the presence of a malignant tumor or the severity thereof, for selecting a therapeutic method therefor or evaluating the effect of the therapeutic method, or for estimating the risk of recurrence of the malignant tumor or the presence or absence of the recurrence, which reagent composition or kit contains a reagent which can determine the concentration and/or quantity of soluble LR11 in a sample originating from a subject and which reagent composition or kit is employed in comparing the determined value with a soluble LR11 value in a sample obtained from a healthy subject group.

The present invention also provides a diagnostic kit for determining the presence of a malignant tumor or the severity thereof, for selecting a therapeutic method therefor or evaluating the effect of the therapeutic method, or for estimating the risk of recurrence of the malignant tumor or the presence or absence of the recurrence, characterized in that the diagnostic kit contains a reagent which can determine the concentration and/or quantity of soluble LR11.

Advantageous Effect of the Invention

According to the method of the present invention, the concentration of soluble LR11 in a sample originating from a patient suspected of the presence of a malignant tumor is measured, and the concentration measured above is compared with the concentration of LR11 measured in a healthy subject, to thereby obtain information useful for determining the presence of a malignant tumor or the severity thereof or for selecting a therapeutic method therefor or evaluating the effect of the therapeutic method. In addition, even after the malignant tumor has been cured, the risk of recurrence of the malignant tumor or the presence or absence of the recurrence can be estimated through continuous monitoring of the soluble LR11 level.

DETAILED DESCRIPTION OF THE INVENTION

The present invention will next be described in detail.

One characteristic feature of the present invention resides in that soluble LR11 is employed as a malignant tumor marker.

The target malignant tumor of the present invention includes a carcinoma and a hematopoietic tumor, which is a type of sarcoma. Examples of the carcinoma include stomach cancer, liver cancer, pancreatic cancer, lung cancer, prostate cancer, bladder cancer, esophageal cancer, breast cancer, cervical cancer, ovarian cancer, colon cancer, colorectal cancer, and gallbladder cancer. Examples of the hematopoietic tumor include acute leukemia, chronic leukemia, and malignant lymphoma such as non-Hodgkin's lymphoma. However, the target malignant tumor is not limited to the above examples.

The determination method of the present invention includes (1) a step of measuring the concentration and/or quantity of soluble LR11 in a sample originating from a subject and (2) a step of comparing the value obtained above with a soluble LR11 value obtained in a healthy subject group.

No particular limitation is imposed on the selection of subject of the present invention, so long as the subject can suffer a malignant tumor. Examples of the subject include human and other mammals such as mouse, rat, rabbit, pig, dog, and cat.

Examples of the sample originating from the subject include blood (serum, plasma), cerebrospinal fluid, lymph fluid, urine, tissues, and cells. Of these, blood (particularly serum) is preferred due to ease in sample preparation.

Also, the sample originating from the subject is preferably a sample derived from an animal (in particular a human subject) which is suspected of having a malignant tumor, more particularly from a human subject who is suspected of having a malignant tumor as a result of examination by use of a conventional tumor marker.

The concentration or quantity of soluble LR11 in the sample derived from a subject is determined by use of a substance having an affinity to soluble LR11. No particular limitation is imposed on the selection of substance having an affinity to soluble LR11, so long as the substance can bind to soluble LR11. Examples of the substance include proteins which specifically bind to soluble LR11 such as apolipoprotein E (apo E), apo E-rich VLDL (β-VLDL), RAP (The 39-40 kDa receptor-associated protein), uPA (urokinase-type plasminogen activator), PAI-1 (type-1 plasminogen activator inhibitor), and uPA-PAI-1 complex (proteins) and anti-soluble LR11 antibodies. Among them, RAP and anti-soluble LR11 antibodies are preferred, with anti-soluble LR11 antibodies being particularly preferred.

The anti-soluble LR11 antibody may be a monoclonal antibody or a polyclonal antibody, so long as the antibody reacts with soluble LR11 purified from serum. However, a monoclonal antibody is preferably employed. The antibody may be produced through a widely known method. In one production procedure of a polyclonal antibody, animals such as mice, rats, hamsters, rabbits, goats, sheep, and chickens are used to be immunized by the immunogen. Anti-serum may be prepared by subcutaneously, intradermally, or intraperitoneally administering an antigen to an animal once or multiple times, and recovering anti-serum from serum. When protein or peptide is used as an antigen, immunization is preferably performed by use of a mixture of an immunogen and an adjuvant exhibiting immunostimulating effect.

The monoclonal antibody may be produced through a known method for producing a monoclonal antibody; e.g., "Monoclonal Antibody" (Hideaki NAGAMUNE and Hiroshi TERADA, Hirokawashoten, 1990) or "Monoclonal Antibody" (Jame W. Golding, 3rd edition, Academic Press, 1996). Also, the monoclonal antibody may be produced through DNA immunization technique (see, for example, Nature 1992 Mar. 12; 356 152-154 or J. Immunol. Methods March 1; 249 147-154).

The antigen employed in production of the antibody may be LR11 protein, a fragment thereof (peptide), or a vector including cDNA encoding LR11 protein. In order to produce a monoclonal antibody which recognizes the high-order structure of LR11, a full-length LR11 vector, a construct including a full-length human LR11 gene, is the most suitable antigen gene for use in immunization. Alternatively, a construct including a part of LR11 sequence may be used as antigen gene for immunization. In one mode of DNA immunization, one or more of the aforementioned gene constructs are subcutaneously injected separately or in combination to animals (mouse, rat, etc.) via any of various transfection methods (e.g., intramuscular injection, electroporation, and gene gun-mediated immunization) for incorporation of the gene construct(s) into cells.

The monoclonal antibody may be produced through a method including culturing hybridomas produced by a conventional method and isolating a target antibody from the culture supernatant; or a method including administering a hybridoma to a mammal compatible with the hybridoma and collecting ascites of the mammal.

If required, the antibody may be further purified before use. Examples of the antibody purification/isolation method include known methods such as salting out (e.g., ammonium sulfate precipitation), gel filtration (e.g., by use of Sephadex), ion-exchange chromatography, and affinity purification (e.g., by use of protein A column).

No particular limitation is imposed on the method for determining soluble LR11 contained in a sample originating from a subject. However, preferably, an immunological method employing an anti-soluble LR11 antibody, a method employing affinity of RAP or the like, or a combination method thereof is preferably employed. Examples of the immunological method of the present invention include immunostaining (western blotting), enzyme-linked immunosorbent assay (ELISA), immunonephelometry (TIA or LTIA), enzyme immunoassay, chemiluminescent immunoassay, and fluorescent immunoassay. Alternatively, sandwich ELISA employing an antibody and a substance having an affinity to LR11 (e.g., RAP) may also be employed for the immunological method. Moreover, a preliminary treatment for eluting a soluble LR11, which comprises a step of absorbing a soluble LR11 contained in a sample into an insoluble carrier bearing a substance having an affinity to LR11 (e.g. RAP), and then washing and eluting the absorbed soluble LR11 by use of appropriate buffer, is preferably employed, since such a pretreatment process enables the removal of protein impurities contained in the sample and the precise assay of soluble LR11.

In addition, a modified ELISA method employing the surfactant pretreatment of a sample, previously established by the present inventors, (Clin. Chem. 2009; 55, 1801-1808) is particularly preferred, since the method attains high precision through a very simple procedure.

In order to obtain quantitative or semi-quantitative values, comparison with reference LR11 quantity/concentration of LR11 is preferably carried out. In this case, the reference LR11 employed in the invention is preferably, for example, serum soluble LR11 having a known concentration, LR11 recovered from cultured cells or culture supernatant of smooth muscle cells or neuroblast cell line, recombinant LR11, or a synthetic peptide used as an immunogen in preparation of the antibody.

Subsequently, the thus-obtained measurement values are compared with the soluble LR11 measurement values of a healthy subject group.

Preferably, the soluble LR11 measurement value of a healthy subject group is determined in advance through the same method as employed in determination of the soluble LR11 measurement value of the aforementioned sample originating from a subject. The reference value employed in the comparison step is preferably obtained by statistically processing soluble LR11 measurement values of the healthy subject group. Preferably, the reference value is statistically determined with respect to each target disorder.

The inventors have found that when a subject has a malignant tumor, a malignant tumor with higher severity, or a risk of recurrence thereof, as described in the Examples hereinbelow, the concentration or quantity of soluble LR11 in a sample originating from the subject is significantly higher than that from a healthy subject group. Therefore, comparison of the concentration of soluble LR11 in a sample originating from the subject or the quantity of soluble LR11 contained in the sample with the reference value enables determination of the presence of a malignant tumor or the severity thereof, selection of a therapeutic method therefor, evaluation of the effect of the therapeutic method, estimation of the risk of recurrence of the malignant tumor, or determination of the presence or absence of the recurrence.

The severity of a malignant tumor is an index for the degree of progress of cancer. In the present invention, in the case of a hematopoietic tumor, the expression "determination of the presence of a malignant tumor or the severity thereof" may refer to classification of the tumor according to the WHO classification, since leukemia and malignant lymphoma are classified therein in detail and the severity thereof is evaluated by WHO. Non-Hodgkin's lymphoma is classified by WHO into "high grade malignancy", "intermediate grade malignancy", and "low grade malignancy" in terms of cell proliferation rate. In this case, the above expression may refer to this classification procedure. Typical examples of Non-Hodgkin's lymphoma include follicular lymphoma, diffuse large B-cell lymphoma, and T-lymphoblastic lymphoma.

Carcinoma is classified according to the TNM classification, which is an internationally accepted stage classification and based on the tumor dimensions and degree of progress, status of metastasis to regional lymph nodes, and the presence of distant metastasis. There is also employed a further stage classification based on the TNM classification, which can provide both the degree of cancer progression and the degree of spreading of cancer. In the case of carcinoma, the above expression may refer to these classification procedures.

In the case where a remission is achieved by remission induction therapy, the intended therapeutic purpose was considered to be attained. Here, the term "remission" refers to, in the case of a hematopoietic tumor, a state in which no leukemia cell or malignant lymphoma is detected in blood or bone marrow.

Selection of a therapeutic method and evaluation of the effect of the therapeutic method can be assessed by monitoring the dimensional changes of the onset tumor. When the concentration of soluble LR11 is not lowered to a normal level after treatment, the risk of recurrence can be estimated to be high, and when the concentration of soluble LR11 rises during an interval stage or after remission achieved by a certain treatment, the possibility of recurrence of a tumor can be evaluated to be high. Furthermore, according to the method of the present invention, prognosis can be predicted. For example, 2 to 3 year survival rate can be predicted.

Moreover, it is preferable to conduct the determination of the presence of malignant tumor, etc., not only with soluble LR11 measurement values but also in combination with a known tumor maker. Examples of such a known tumor marker include α-fetoprotein, CEA, CA19-9, CA125, PIVKA-II, SCC, SLX, elastase I, cytokeratin-19 fragment, and DUPAN2.

The kit of the present invention is characterized by containing a reagent which can determine the soluble LR11. Examples of such a reagent preferably include, but not limited to, a reagent which includes a substance which has affinity to a soluble LR11, for example, anti-soluble LR11 antibody or the above-described proteins such as RAP. The kit may include other elements than such reagents, for example reaction buffer and a reactor required for detection of soluble LR11. The kit of the present invention may further include data of soluble LR11 measurement values in the healthy subjects and a protocol for performing a comparison of soluble LR11 measurements with the data.

EXAMPLES

The present invention will next be described by way of examples, which should not be construed as limiting the invention thereto.

Referential Example 1

Production of Anti-Soluble LR11 Monoclonal Antibody through DNA Immunization (1) Construction of Expression Vector A gene fragment, which is an amino acid sequence (1000 to 1550) (SEQ ID NO: 1) and which forms a part of LR11 full-length gene (Q92673), was incorporated into a mammal expression vector having an FLAG tag (pcDNA3.1, product of Invitrogen). The expression vector includes a DNA fragment encoding a peptide formed of a GPI anchor sequence derived from human alkaline phosphatase. The vector was employed as LR11 [1000-1550] vector.

(2) Confirmation of CHO Expression Product

Whether or not a target gene product is expressed on cell membranes as expected by means of the thus-constructed LR11 [1000-1550] vector was confirmed before immunization through a transient transfection experiment employing CHO cells (Chinese hamster ovary cells). Specifically, on the day before immunization, CHO cells were plated on a 6-well plate at $1\times10^6$ cells/well and cultured overnight at 37° C. under 5% $CO_2$. On the day of transfection, a plasmid dilution (3 μg plasmid DNA+500 μL D-MEM) and lipofectamine 2000 dilution (9 μL lipofectamine 2000+500 μL D-MEM) were sufficiently mixed together in a polystyrene round tube, and incubation was performed at room temperature for 20 minutes. After the culture supernatant of the CHO cells previously plated was removed, the incubation product was gently added to the plate so that removal of the CHO cells was prevented. Further incubation was performed for five hours at 37° C. under 5% $CO_2$, and the supernatant was removed. A D-MEM medium containing 5% FCS was added to the plate, and the CHO cells were cultured for 24 hours at 37° C. under 5% $CO_2$. On the following day, the cells were removed from the plate by use of dissociation buffer (product of Invitrogen) and were subjected to flow cytometry (FCM). FCM analysis was performed as follows. Specifically, in primary antibody reaction, the cells were reacted with ANTI-FLAG (registered trademark) M2 antibody (product of SIGMA) in 3% FCS-containing phosphate buffer (pH: 7.2 (PBS)) at 4° C. for 30 minutes. In secondary antibody reaction, the cells were washed with 3% FCS-containing PBS, and then reacted with PE-labeled anti-mouse IgG antibody (product of Beckman) in 3% FCS-containing PBS at 4° C. for 30 minutes. Thereafter, the cells were washed with 3% FCS-containing PBS, and were suspended in PBS containing an appropriate amount of 3% FCS. The suspension was subjected to flow cytometry. The analysis revealed that the target gene product was expressed on cell membrane surfaces by means of the constructed LR11 [1000-1550] vector.

(3) Production of Antibody Through DNA Immunization

In the DNA immunization, the LR11 [1000-1550] vector produced in (1) above or gold particles sensitized with the LR11 [1000-1550] vector were subcutaneously injected to immunization animals (mice or rats) by means of a gene gun, to thereby incorporate the vector into cells. More specifically, the LR11 [1000-1550] vector (200 μg/25 mg-gold particles) was administered to each animal by means of Helios (registered trademark) Gene Gun Optimization Kit (product of Bio-Rad, USA) according to an instruction manual attached thereto. Immunization was performed four times with intervals of two weeks. At the fourth immunization, a small amount of anti-serum was sampled. The anti-serum was 1,000-fold diluted with 3% FCS-containing PBS, and the anti-serum dilution was employed as a primary antibody in FCM analysis. FCM analysis was also performed by use of CHO cells in which a target gene product was transiently expressed (produced in (2)) (hereinafter may also be referred to as forced expression cells), whereby the antibody titer was confirmed to be elevated. The monoclonal antibody was produced through a conventional cell-fusion technique. Specifically, an animal which had undergone final boosting twice was dissected, and antibody-producing cells were isolated through a routine method. The thus-isolated cells were fused with mouse myeloma cells, to thereby prepare antibody-producing hybridoma strains. These hybridomas were cultured, and a portion of culture supernatant was sampled. Through enzyme immunoassay and FCM employing the forced expression cells, a sample which reacted with antigen protein and did not react with non-antigen protein was selected. Enzyme immunoassay employing the forced expression cells was performed as follows. Firstly, forced expression cells were immobilized to a 96-well plate and reacted with the hybridoma culture supernatant as a primary antibody. After completion of primary antibody reaction, the plate was washed, and a secondary antibody was added thereto. The secondary antibody is an antibody which can recognize mouse immunoglobulin or rat immunoglobulin of the primary antibody and which has been labeled with horse radish peroxidase (HRP). After completion of reaction, a fluorescent substrate corresponding to the enzyme with which the secondary antibody had been labeled was added, and the plate was analyzed by means of a fluorescent plate reader.

Then, cloning was performed though a limiting dilution technique, whereby a hybridoma consistently exhibiting high antibody titer was selected as a monoclonal antibody-producing hydridoma strain.

Subsequently, the monoclonal antibody was mass-produced from ascites as follows. To nude mice which had been treated in advance with pristan (0.5 mL), cloned hybridoma cells ($1\times10^6$ to $3\times10^6$) in phosphate-buffered saline (pH: 7.4) (0.5 mL) were intraperitoneally injected. About two weeks later, ascites was collected from the nude mice, and the monoclonal antibody was affinity-purified with protein A.

The two typical anti-soluble LR11 monoclonal antibodies (mouse-derived M3, rat-derived R14) produced through DNA immunization were found to react with soluble LR11 derived from human serum and rabbit serum.

Referential Example 2

Purification of Soluble LR11 Recovered from Rabbit Serum

E. coli which had been transformed with a vector carrying a human RAP gene, pGEX2T (product of GE Healthcare Bioscience) (i.e., E. coli DH5α) was cultured, and the cultured product was centrifuged, to thereby recover cells thereof. The cells recovered from the culture (3 L) were suspended in PBS (pH: 7.2) containing 0.2% lysozyme and 0.5% TritonX-100, and the cells were broken through ultrasonication. The RAP/GST fusion protein contained in the centrifugation supernatant of the cell broken liquid was caused to pass through Glutathione Sepharose 4 FF (product of GE Healthcare Bioscience) (10 mL), to thereby be adsorbed on the gel, and the gel was washed with PBS (pH: 7.2 (hereinafter the same pH applies unless otherwise specified)), to thereby prepare RAP-Sepharose resin. The RAP-Sepharose resin (10 mL) was admixed with rabbit serum (1 L), and the mixture was allowed to react overnight at 4° C. under mild stirring conditions. After completion of reaction, the RAP-Sepharose resin was packed to the column and washed with PBS. Then, rabbit soluble LR11 was eluted from the resin by use of citrate buffer (pH: 5.0), and the eluent was concentrated and the concentrated eluate was dialyzed against PBS. The thus-obtained liquid was mixed with a Sepharose resin chemically bonded with an anti-soluble LR11 monoclonal antibody (M3), and the mixture was allowed to react overnight at 4° C. under mild stirring conditions. Then, rabbit soluble LR11 was eluted from the resin by use of citrate buffer (pH: 3.0). The eluate was concentrated and separated/purified through gel-filtration chromatography (Supedex 200; product of GE Healthcare Bioscience) by use of PBS. The soluble LR11-eluted fractions were combined and concentrated, to thereby provide purified rabbit soluble LR11. The soluble LR11 protein content was determined by separating LR11 protein through SDS polyacrylamide electrophoresis and detecting soluble LR11 protein through Ag staining. Also, the purified rabbit soluble LR11 level was calculated on the basis of coloring intensity of a bovine serum albumin (BSA) band of known concentration. The LR11 level was employed as a calibrator for use in ELISA performed in Referential Example 3 hereinbelow.

Referential Example 3

Detection of Soluble LR11 in Serum Through ELISA

The anti-soluble LR11 monoclonal antibody (M3) was diluted with PBS to 10 μg/mL, and the antibody liquid was added to a microplate (product of NUNC) in a volume of 100 μL/well. The antibody was immobilized at room temperature for two hours. The microplate was washed with PBS containing 0.05% Tween 20 (PBST), and PBST containing 1% BSA (BSA-PBST) was added to the microplate in a volume of 200 μL/well, and blocked at room temperature for one hour. Separately, human serum was 11-fold diluted with a sample treatment mixture (3:1) of 7% MEGA-9 (product of Dojindo Laboratories) and HBR (product of Scantibodies Laboratory). Also, the rabbit-derived soluble LR11 purified in Referential Example 2 was serially diluted with the aforementioned sample treatment mixture, to thereby prepare a calibrator. Each of the above diluted samples was added to the microplate in a volume of 100 μL/well and was allowed to react overnight at room temperature. Then, biotin-labeled anti-soluble LR11 monoclonal antibody (R14) was diluted with BSA-PBST to a concentration of 0.4 μg/mL, and the diluted antibody was added to the microplate in a volume of 100 μL/well, followed by reaction at room temperature for four hours. After washing of the microplate with PEST, peroxidase-labeled streptavidin (product of PIERCE) diluted with BSA-PBST to 0.2 μg/mL was added to the microplate in a volume of 100 μL/well, followed by reaction at room temperature for one hour. After washing of the microplate with PBST, a TMB substrate liquid was added to the microplate in a volume of 100 μL/well, and the contents in the microplate plate were allowed to develop color at room temperature for 30 minutes. Then, the coloration was stopped by adding 1.5N sulfuric acid to the microplate in a volume of 100 μL/well, and the absorbance was measured by means of a microplate reader (Abs. 450 nm). The soluble LR11 level of the sample was calculated by the calibration curve obtained from measurements of the calibrator. Through multiplying the results by the dilution factor, the corresponding human serum soluble LR11 concentration was obtained.

Example 1

Soluble LR11 as a Hematopoietic Tumor Marker

From 81 people who were diagnosed as having a hematopoietic tumor in a first medical examination, serum samples were collected. The soluble LR11 concentration of each sample was determined and compared with the serum soluble LR11 level in a healthy subject group (87 people with no lipid abnormality).

The disease types of the 81 people who were diagnosed as having a hematopoietic tumor include acute lymphocytic leukemia (6), acute myeloid leukemia (11), chronic lymphocytic leukemia (5), chronic myeloid leukemia (7), Hodgkin's lymphoma (5), non-Hodgkin's lymphoma (26), myelodysplastic syndromes (4), multiple myeloma (8), and POEMS syndrome (9). The serum soluble LR11 concentration was determined through the ELISA technique employed in Referential Example 2. In consideration of the of soluble LR11 levels in healthy subjects, provisional cut-off value was set to 20 ng/mL. Table 1 shows the number of cases and the averaged LR11 value in each disease case. As is clear from Table 1, patients who exhibited a soluble LR11 concentration higher than the cut-off value were frequently found, particularly in the cases of leukemia and non-Hodgkin's lymphoma, as compared with the healthy subjects.

TABLE 1

|  | <20 ng/mL group Average value(n) | ≥20 ng/mL group Average value (n) |
|---|---|---|
| Healthy subjects (n = 87) | 9 ng/mL (n = 87) | — |
| Acute lymphocytic leukemia (n = 6) | 17 ng/mL (n = 1) | 134 ng/mL (n = 5) |
| Acute myeloid leukemia (n = 11) | 10 ng/mL (n = 6) | 28 ng/mL (n = 5) |
| Chronic lymphocytic leukemia (n = 5) | 11 ng/mL (n = 2) | 127 ng/mL (n = 3) |
| Chronic myeloid leukemia (n = 7) | 13 ng/mL (n = 4) | 32 ng/mL (n = 3) |
| Hodgkin's lymphoma (n = 5) | 10 ng/mL (n = 5) | — |
| Non-Hodgkin's lymphoma (n = 26) | 11 ng/mL (n = 14) | 45 ng/mL (n = 12) |
| Myelodysplastic syndromes (n = 4) | 8 ng/mL (n = 4) | — |
| Multiple myeloma (n = 8) | 11 ng/mL (n = 7) | 25 ng/mL (n = 1) |
| POEMS syndrome (n = 9) | 11 ng/mL (n = 9) | — |

Example 2

Figure 1:
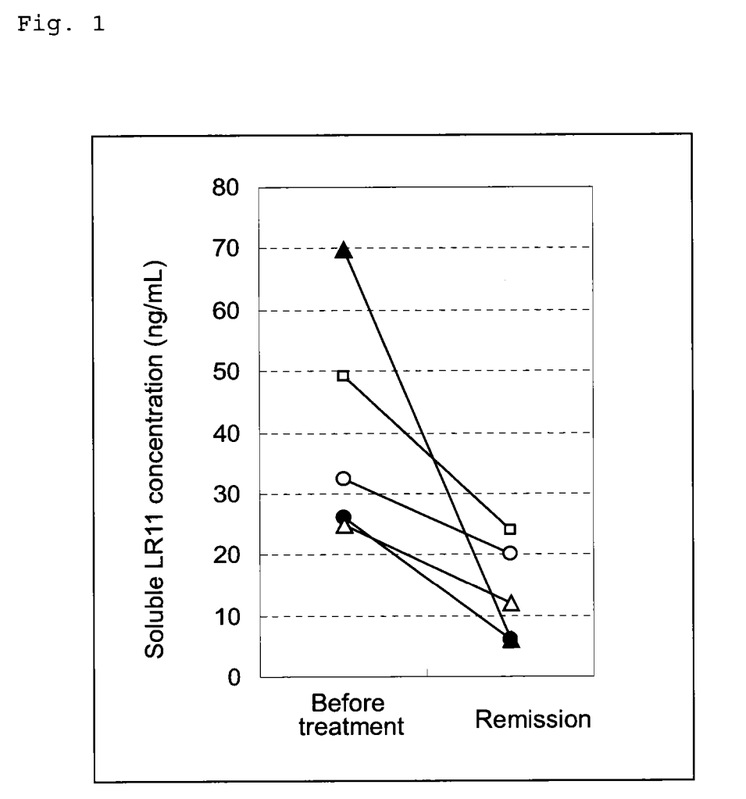
FIG. 1 A graph showing the monitored result of the changes in serum soluble LR11 levels in acute myeloid leukemia patients from before treatment to remission.

Application of Soluble LR11 Value to Evaluation of the Effect of the Therapeutic Method In Example 1, five patients were diagnosed as having acute myeloid leukemia and showed high soluble LR11 concentration. FIG. 1 shows the monitored results of the changes in serum soluble LR11 levels from before treatment to remission of these five patients. The soluble LR11 concentrations were lowered to fall within a normal range (20 ng/mL) by virtue of the treatment. Therefore, in a hematopoietic tumor patient, the presence of a tumor or the severity thereof is considerably correlated to the rise in blood soluble LR11 of the patient.

Example 3

Prediction of the Risk of Recurrence

Among the nine patients who had been diagnosed as having a hematopoietic tumor and who entered a remission stage through treatment but suffered the recurrent tumor, five patients exhibited a soluble LR11 concentration higher than the cut-off value (20 ng/mL) at recurrence. The five of nine patients (>50%) had acute lymphocytic leukemia (1), acute myeloid leukemia (2 in 5), chronic lymphocytic leukemia (1), and non-Hodgkin's lymphoma (1 in 2). Therefore, in hematopoietic tumor patients, the risk of recurrence of a hematopoietic tumor can be estimated, or the possibility of recurrence thereof can be determined through monitoring the soluble LR11 level of a target patient.

Example 4

Soluble LR11 as a Biomarker in Carcinoma

In each carcinoma case, five patients were chosen at random, and the serum soluble LR11 concentration of each patient was measured. Similar to Example 1, provisional cut-off value was set to 20 ng/mL. In all carcinoma cases, many patients exhibited a soluble LR11 concentration higher than the cut-off value (Table 2).

TABLE 2

|  | <20 ng/mL group Average value (n) | ≥20 ng/mL group Average value (n) |
|---|---|---|
| Liver cancer | 16 ng/mL (n = 2) | 26 ng/mL (n = 3) |
| Pancreatic cancer | 13 ng/mL (n = 2) | 24 ng/mL (n = 3) |
| Colon cancer | 15 ng/mL (n = 4) | 37 ng/mL (n = 1) |
| Colorectal cancer | 10 ng/mL (n = 3) | 34 ng/mL (n = 2) |
| Gallbladder cancer | 14 ng/mL (n = 1) | 36 ng/mL (n = 4) |

Example 5

Estimation of Remission Rate

Figure 2:
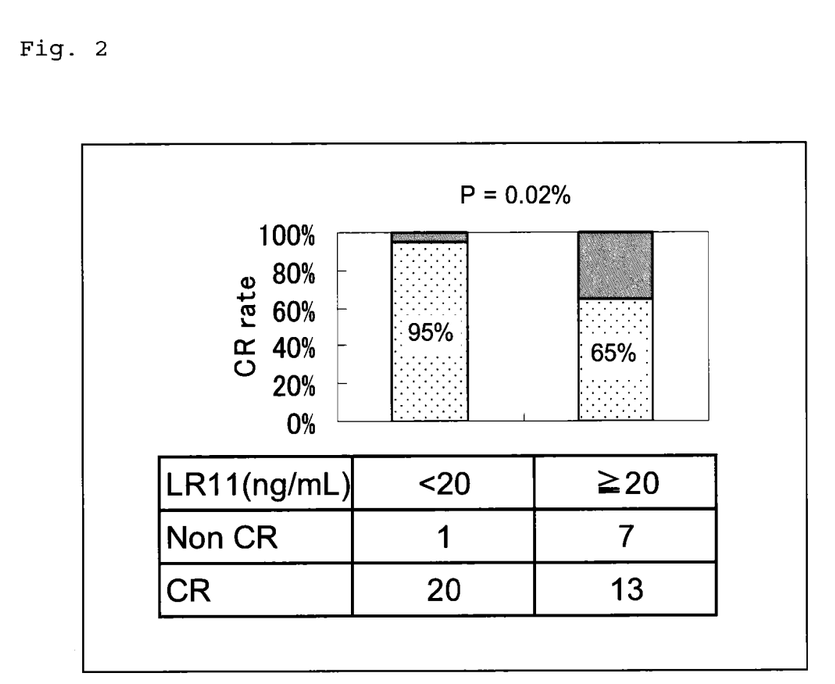
FIG. 2 A graph showing percentage of acute myeloid leukemia patients having a low soluble LR11 protein level (<20 ng/mL) in remission and acute myeloid leukemia patients having a high soluble LR11 protein level (≥20 ng/mL) in remission.

Among the 41 patients who were diagnosed as having acute myeloid leukemia and who received a treatment, in the normal serum soluble LR11 concentration group (<20 ng/mL), 20 of 21 patients reached complete remission (CR) through the treatment (high remission rate: 95%), whereas in the high soluble LR11 concentration group (≥20 ng/mL), only 13 of 20 patients reached complete remission through the treatment (significantly low remission rate: 65%) (see FIG. 2). Therefore, through measuring the soluble LR11 levels of a hematopoietic tumor patient, the possibility of remission through the treatment thereof can be predicted.

Example 6

Relationship Between Soluble LR11 and Survival Rate

Figure 3:
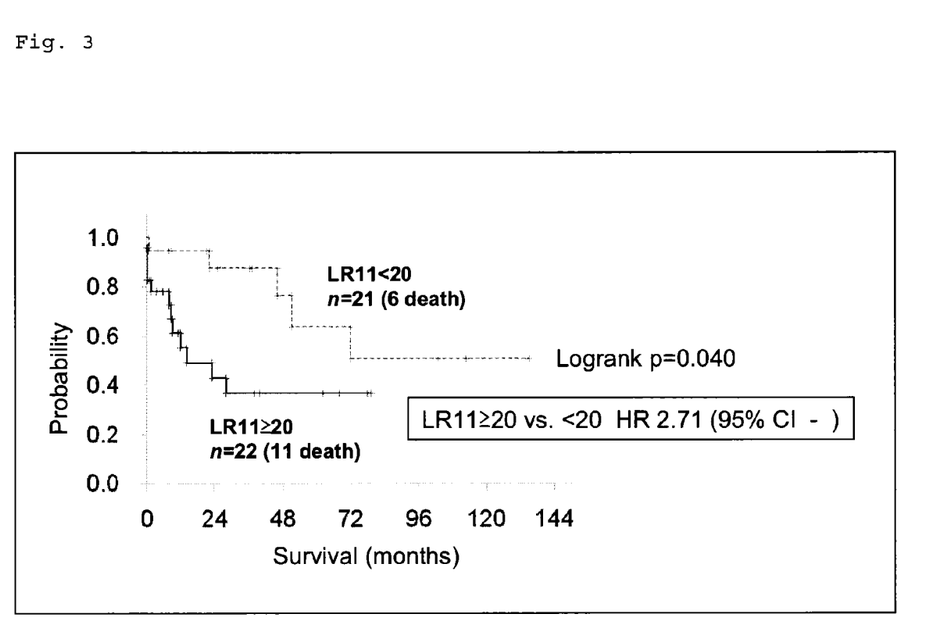
FIG. 3 A graph showing overall survival rates of acute myeloid leukemia patients having a low level of soluble LR11 protein (<20 ng/mL) and acute myeloid leukemia patients having a high level of soluble LR11 protein (20 ng/mL).

FIG. 3 shows overall survival (OS) rates of 21 acute myeloid leukemia patients exhibiting low serum soluble LR11 concentration (<20 ng/mL) and 22 acute myeloid leukemia patients exhibiting high serum soluble LR11 concentration (≥20 ng/mL). As is clear from FIG. 3, soluble LR11 level was found to be an important prognostic factor particularly in a short period (2 to 3 years).

The invention claimed is:

1. A method of treating a malignant tumor in a subject, the method comprising:
    obtaining a sample from the subject having a malignant tumor,
    measuring a concentration, quantity, or both, of soluble LR11 in the sample with at least one substance having an affinity to soluble LR11 which is selected from the group consisting of apolipoprotein E, apo E-rich VLDL, RAP, urokinase-type plasminogen activator, PAI-1 (type-1 plasminogen activator inhibitor), uPA-PAI-1 complex and anti-soluble LR11 antibodies,
    comparing the concentration, quantity, or both with a soluble LR11 measurement value in a healthy subject group, and
    treating the malignant tumor in the subject when the concentration, quantity, or both, of soluble LR11 in the sample is higher than the soluble LR11 measurement value in the healthy subject group.

2. The method of claim 1, wherein the malignant tumor is a hematopoietic tumor or a carcinoma.

3. The method of claim 2, wherein the malignant tumor is a hematopoietic tumor selected from the group consisting of leukemia and malignant lymphoma.

4. The method of claim 3, wherein the malignant tumor is a leukemia selected from the group consisting of acute leukemia and chronic leukemia.

5. The method of claim 3, wherein the malignant tumor is non-Hodgkin's lymphoma.

6. The method of claim 2, wherein the malignant tumor is a carcinoma selected from the group consisting of stomach cancer, liver cancer, pancreatic cancer, lung cancer, prostate cancer, bladder cancer, esophageal cancer, breast cancer, cervical cancer, ovarian cancer, colon cancer, colorectal cancer, and gallbladder cancer.

7. The method of claim 1, wherein the sample from the subject is at least one substance selected from the group consisting of blood, serum, plasma, cerebrospinal fluid, and urine.

8. The method of claim 1, wherein the substance having an affinity for LR11 is an anti-soluble LR11 antibody.

9. The method of claim 8, wherein the anti-soluble LR11 antibody is a polyclonal antibody.

10. The method of claim 8, wherein the anti-soluble LR11 antibody is a monoclonal antibody.

* * * * *